United States Patent [19]

Khan

[11] Patent Number: 5,347,057
[45] Date of Patent: Sep. 13, 1994

[54] METHOD FOR OXIDATION OF METHANE AND OTHER HYDRO-CARBONS

[76] Inventor: Mirza M. T. Khan, 3850 Downers Dr., Downers Grove, Ill. 60515

[21] Appl. No.: 8,185

[22] Filed: Jan. 25, 1993

[51] Int. Cl.$^5$ ..................... C07C 29/50; C07C 31/04
[52] U.S. Cl. ................... 568/910; 562/493; 568/399; 568/952
[58] Field of Search ............. 568/910, 399, 952; 562/493

[56] References Cited

U.S. PATENT DOCUMENTS

| | | | |
|---|---|---|---|
| 2,007,116 | 7/1930 | Walker | 568/910.5 |
| 4,618,732 | 10/1986 | Gesser | 568/910 |
| 4,895,680 | 1/1990 | Ellis | 568/910 |
| 4,895,682 | 1/1990 | Ellis | 568/910 |
| 4,898,989 | 2/1990 | Ellis | 568/910 |
| 4,918,249 | 4/1990 | Durante | 568/910 |
| 4,982,023 | 1/1991 | Han | 568/910 |
| 5,012,029 | 4/1991 | Han | 568/910 |
| 5,077,394 | 12/1991 | Dolphin et al. | 568/910 |
| 5,091,354 | 2/1992 | Ellis | 568/910 |
| 5,118,886 | 1/1992 | Ellis | 568/910 |
| 5,132,472 | 7/1992 | Durante | 568/910 |
| 5,149,880 | 9/1992 | Sawyer et al. | 568/910 |

OTHER PUBLICATIONS

P. Taylor, D. Dolphin, and T. Traylor, J. Chem. Society Chem. Comm. 279 (1984).
J. Groves, W. Kruper, Jr., R. Hanshalter, J. Am. Chem. Society 102, 6377 (1980).
R. Smegal and C. Hill, J. Am. Chen. Society 105, 3515 (1983).
J. D. Vincent, J. C. Huffman, G. Chiston, Q. Li, M. A. Nancy, D. N. Hendrickson, R. H. Fong and R. H. Fish, J. Am. Chem. Society 110, 6898 (1988).
C. Chen and D. T. Sawyer, J. Am. Chem. Society 112, 8212 (1990).
M. M. Taqui Khan, Ch. Sreelata, S. A. Mirza, G. Ramachandriah, and S. H. R. Abdi, Inorg. Chem. Acta. 154, 103 (1988).

*Primary Examiner*—Joseph E. Evans
*Attorney, Agent, or Firm*—Welsh & Katz, Ltd.

[57] ABSTRACT

This invention teaches the oxidation of alkanes and cycloalkanes in the presence of air or oxygen and a ruthenium metal complex catalyst containing an end or bridged-oxo group with a liquid L and carboxylato groups. This oxidation process results in very high yields, utilizes very little energy and has a high catalyst turnover rate.

16 Claims, No Drawings

METHOD FOR OXIDATION OF METHANE AND OTHER HYDRO-CARBONS

BACKGROUND OF THE INVENTION

1. Field of the Invention

This invention relates to a novel process for the oxidation of methane and a wide range of hydrocarbons in the liquid phase in the presence of air or oxygen catalyzed by complexes of ruthenium activated by the presence of an end-or bridged oxo group along with carboxylato groups. This process provides a high yield with good catalytic turnover efficiency.

2. Background of the Invention

The oxidation of alkanes such as methane, ethane, propane, butane and the like can be difficult to achieve. Methane can be especially difficult to oxidize. Many methods have been developed to oxidize methane and other hydrocarbons. However, these methods generally produce very low yields of oxidation product and utilize expensive catalysts which must be replenished frequently. The use of metalloporphyrin catalysts such as Fe(TPP)Cl and Mn(TPP)Cl (where TPP=the dianion of 5,10,15,20-tetraphenylporphine) with iodosyl benzene, sodium hypochlorite and alkyl hydroperoxides or other costly nonregenerative oxidants has been reported. [P. Traylor, D. Dolphin and T. Traylor, *J. Chem. Soc. Chem. Comm.*, 279 (1984), J. Groves, W. Kruper, Jr., R. Hanshalter, *J. Am. Chem. Soc.* 102, 6377 (1980), J. Smegal and C. Hill, Ibid, 105, 3515 (1983).] Oxidation of a variety of hydrocarbons other than methane has been achieved by the use of the binuclear Fe(III)-$\mu$-oxo-$\mu$-acetate complexes in the presence of the oxidant, t-butyl hydroperoxide and $O_2$. [J. B. Vincent, J. C. Huffman, Chiston, Q.Li, M. A. Nancy, D. N. Hendrickson, R. H. Fong, R. H. Fish. Ibid, 110, 6898 (1988)]. [C. Chin and D. T. Sawyer, Ibid 112, 8212 (1988)]. These methods are expensive and the reagents are nonregenerative.

Azide-activated complexes of several metals in the presence of ligands such as TPP, and acetylacetonates and air or molecular oxygen have been used to catalyze the oxidation of isobutane, propane and cyclohexane at 70°–180° C. and 20–170 atmospheres in the liquid phase. The catalysts are inactive in the absence of the azide. [U.S. Pat. Nos., 4,895,680 and 4,895,682].

Heteropoly acids with site specific framework have also been used for the oxidation of alkanes in the liquid phase in the presence of oxygen at 125°–175° C. and 170 atmospheres. With such a method propane can be oxidized to acetone and isopropyl alcohol [U.S. Pat. Nos., 5,091,354 and 4,898,989]. Cyano-substituted and nitro-substituted metalloporphyrins have been used for the oxidation of isobutane to isobutyl alcohol at 70°–180° C. and about 25 atmosphere of pressure.

In these systems, the ligands are costly compounds and the recyclability of the catalysts remains questionable. In addition, although methane is included in the general list of hydrocarbons that can be oxidized, the oxidation of methane is not specifically discussed or illustrated. [U.S. Pat. Nos., 5,118,886 and 5,120,882].

The gas phase oxidation of natural gas to methanol by molecular oxygen in the gas phase has been disclosed by Walker et al. [U.S. Pat. No. 2,007,116] and by Gesser et al. [U.S. Pat. No. 4,618,732]. In the latter case, a 13% conversion of natural gas (composition not mentioned) was claimed at 300°–500° C. and 10–100 atmospheres. V. A. Durante et al. [U.S. Pat. Nos. 4,918,249 and 5132472] used silicometallates as catalysts for the gas phase oxidation of methane to methanol at 300°–600° C. and 10–70 atmospheres. A 7% conversion of methane to the oxidation products methanol and $CO_2$ was reported. With a reaction column filled with sand or inert refractory inorganic particles, Scott Hans [U.S. Pat. No. 4,982,023] disclosed a 5.5% conversion of methane to methanol at 300°–500° C. and 10–100 atmospheres. With a ZSM-5 packing, a direct conversion of methane to aromatics was reported at 300°–500° C. and 5–100 atmospheres [U.S. Pat. No. 5,012,029].

It is therefore to be noted that except for the gas phase oxidation of methane to methanol, which involves large energy inputs and low yields, a truly catalytic low energy liquid phase oxidation of methane to methanol has not yet been achieved.

It is therefore an object of this invention to provide a truly catalytic process for the oxidation of methane and other hydrocarbons to alcohols, ketones and other such products, which uses air or oxygen, and a metal coordination complex as a catalyst, and which requires low energy input, produces high conversion rates and has high product efficiency.

Another object of this invention is to provide a process for oxidation of methane and other hydrocarbons where a truly catalytic cycle is achieved with the active catalyst having a high turnover efficiency.

A further object is to provide a process for oxidation of methane and other hydrocarbons where there is no need for the addition of expensive compounds to regenerate the catalyst or for the use of non-regenerable oxidants.

DESCRIPTION OF THE INVENTION

This invention involves a process for the economical and efficient oxidation by hydrocarbons. This invention is particularly applicable to the oxidation of methane to methanol, which is known to be more difficult to oxidize than other alkanes. The invention is however, equally effective for the oxidation of other classes of hydrocarbons.

Although the process is effective for a wide variety of hydrocarbons, it is particularly effective for the oxidation of alkanes, cycloalkanes and related compounds, including straight chain and branched chain hydrocarbons with 1 to 15 carbon atoms. The preferred hydrocarbons have 1 to 10 carbon atoms, such as methane, ethane, propane, butane, isobutane, hexanes, and heptanes; and, cyclic hydrocarbons with 5 to 10 carbon atoms such as cyclopentane, cyclohexane, cyhcloheptane, cyclooctane and adamantine. Aromatic hydrocarbons such as toluene, xylene and ethylbenzene can also be oxidized, specifically on the side chain.

The oxidation products are known alcohols or ketones that have several applications. Methanol, the product of the oxidation of methane, is particularly important as a petroleum additive, source of $C_1$ chemicals and as a solvent. The process of this invention is also applicable for the further oxidation of partially oxidized hydrocarbons to organic acids.

Thus, this invention is applicable to a broad range of hyrdrocarbons which may contain various substituents to enhance the rate of oxidation. The nature of these substituents may be decided by users well versed in the art. The oxidation of methane represents the most important and preferred application of the invention.

DETAILED DESCRIPTION OF THE INVENTION

The oxidation of hydrocarbons by this process of this invention is catalyzed by various ruthenium coordination complexes. The active catalytic species may best be defined as an end-oxo or bridged-oxo complex with the following structures:

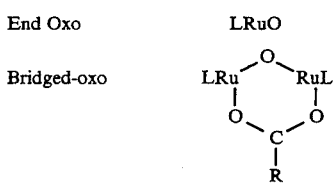

where L is a Schiff base such as saloph, hydroxy-Acetoph, salen, accac or the like or is a substituted Schiff base, as shown in the following structures:

The Schiff ligands used in the investigation

1. Bis(salicylaldehyde)-o-phenylenediamine
   Y = H, Saloph
   X = OCH$_3$, H, F$^-$ 2. [Hydroxy-Acetoph]
   Y = CH$_3$
   X = OCH$_3$, H, F

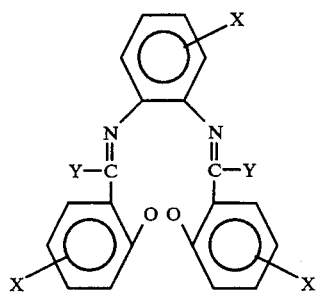

3. Bis (salicylaldehyde)-ethylenediamine (Salen)
   X = H, F, CH$_3$
   Y = H, F, OCH$_3$

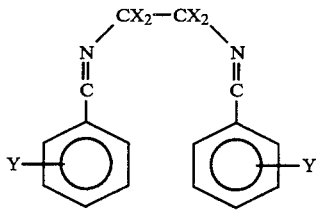

4. Bis(acetylacetone)-ethylenediamine (accac)
   X = H, F, R = CH$_3$, C$_6$H$_5$

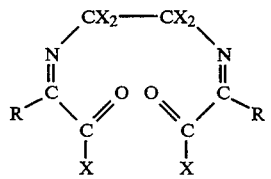

In 3 and 4, CX$_2$ can also be (CX$_2$)$_3$ or (CX$_2$)$_4$

The end-oxo complexes LRu=O can be synthesized by the following steps. The chloro Schiff base complex RuLCl$_2$ and iodosyl benzene are dissolved in equimolar quantities in waterdioxan/dimethyl formamide (DMF). The resulting solution is stirred at room temperature for six to eight hours. The iodobenzene liberated is extracted with diethyl ether. The solution is then evaporated to a small volume and the oxo complexes precipitated with diethyl ether.

The starting complex RuLCl$_2$ is obtained by refluxing equimolar quantities of the Schiff base ligand L and the complex K$_2$[RuCl$_5$.H$_2$O] (synthesized from RuCl$_3$.xH$_2$O and concentrated HCl [M.M.Taqui Khan, Ch Sreelata, S.A.Mirza, G.Ramachandriah and S.H.R.Abdi, Inorg. Chim. Acta, 154,103(1988)]) in ethanol for about 10-15 hours in an argon atmosphere. After completion of the reaction as checked by TLC, the solution was filtered in an argon atmosphere and concentrated to about one-quarter of its volume. The RuLCl$_2$ is precipitated by diethyl ether or ethylacetate and then recrystallized from ethylacetate.

The dimeric bridged-oxo ruthenium complex can be synthesized by refluxing one mole of RuCl$_3$.x H$_2$O in a 1:1:1 water/carboxylic acid/ethanol mixture with two moles of the Schiff base for 30 to 60 minutes, until a solid is obtained. The solid is then dissolved in the minimum amount of water on warming and left overnight until a purple solution is obtained. The bridged-oxo ruthenium complex is then precipitated with acetone-ether. Yields are 30-50%.

Oxidation according to this invention is carried out in a liquid phase, mixed solvent system such as water/acetone, water/acetonitrile and/or acetic acid, which is inert to the conditions of the reaction and to oxidation by molecular oxygen. The temperature can range between 20°-60° C. The pressure may range from 5 to 20 atmospheres. In the preferred embodiment of this invention, the temperature equals 30° C. and the pressure is 14 atmospheres.

Depending upon whether the hydrocarbon is a solid, liquid or gas, it is either dissolved in the mixed solvent system or is bubbled through the solvent together with air or oxygen. The catalyst is then added. A concentration of range $10^{-3}$ to $10^{-6}$ moles of catalyst in solution is sufficient to yield the desired product. The catalyst forms a homogeneous solution with the solvent and is not destroyed during several turnovers of the reaction. The time of reaction is generally from 30 minutes to 30 hours. The preferred reaction time is 1 to 5 hours.

The nature of the solvent, though not critical, can effect the time of reaction. In gases, where the solubility of the gas in the solvent is an important parameter, the specific solvent used will have a greater role in the reaction rate. Solubility will also depend on the temperature and pressure. Optimum conditions need to be determined for each case. Water/acetone is the preferred solvent for the oxidation of methane.

The ratio of the various reactants can vary widely and is not critical. The concentration of the catalyst can range from $10^{-3}$ to $10^{-6}$ moles of catalyst per mole of hydrocarbon used. The amount of oxygen can vary between $10^{-3}$ to $10^{-2}$ moles O$_2$ per mole of substrate. Care must be taken since some of the factors may fall within explosive limits.

The oxidation process of this invention can also be carried out without a solvent. The hydrocarbon to be oxidized is placed in contact with air or molecular oxygen and the ruthenium metal catalyst.

EXAMPLE

Oxidation of Methane

An oxo-bridged dimeric ruthenium complex, described above where the Schiff base, L is saloph and R is CH$_3$, was prepared by the procedure described above. This complex was dissolved in a 1:1 water-acetone solution to a concentration of about $10^{-3}$M. The required quantity of solution was transferred to a glass lined Parr reactor. The reactor was pressurized with a $CH_4:O_2$ mixture (oxygen 20%) to 14 atmospheres. The temperature was 30° C. The mixture was stirred and the methanol produced was analyzed chromatographically every hour. A yield of 0.12 moles of methanol was obtained after 12 hours. The conversion of the methane to methanol by this process is 80%, the maximum reported so far. The amount of $CO_2$ formed was 0.01 moles, showing more than 90% efficiency in the conversion to methanol. The catalyst turnover rate for this reaction was 12 moles of methanol produced per mole of the catalyst per hour.

What is claimed is:

1. A process for selectively oxidizing alkanes or aromatic hydrocarbons where the products of oxidation are alcohols, ketones or mixtures thereof comprising the steps of:
   (a) placing the alkane or aromatic hydrocarbon in contact with oxygen, and
   (b) adding a ruthenium metal complex catalyst activated by an "end-oxo" group, said catalyst having the formula LRu=O, where L is a Schiff or a substituted Schiff base; or a "bridging -oxo" group, said catalyst having the formula:

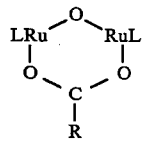

wherein L is a Schiff base or a substitute Schiff base and R is H, or an alkyl (C<10) or an aryl (C<30).

2. The process as claimed in claim 1 wherein said alkane has between 1 and 15 carbon atoms.

3. The process as claimed in claim 1 wherein said alkane has between 1 and 10 carbon atoms.

4. The process a claimed in claim 1 wherein the aromatic hydrocarbons have side chains that selectively oxidized and where the products of oxidation are alcohols, ketone or acids, or a mixture thereof.

5. The process as claimed in claim 1, wherein the alkane or aromatic hydrocarbon is first added to a mixed aqueous-organic solvent.

6. The process as claimed in claim 5, wherein the reaction temperature is between 20°-60° C. and the pressure is between 5-20 atmospheres.

7. The process as claimed in claim 6, wherein said temperature is 30° C. and said pressure is 14 atmospheres.

8. The process as claimed in claim 1, wherein said ruthenium metal complex catalyst is coordinated with a Schiff base or a substituted Schiff base.

9. The process as claimed in claim 8, wherein said ruthenium metal complex catalyst is activated by said end-oxo or said bridging-oxo group and by at least one carboxylato group.

10. The process as claimed in claim 9, wherein said alkane is methane.

11. The process as claimed in claim 10, wherein said methane is first added to in a mixed aqueous-organic solvent.

12. The process as claimed in claim 11, wherein the temperature is 30° C., and the pressure is 14 atmospheres of $CH_4:O_2$.

13. A process for selectively oxidizing alkanes or aromatic hydrocarbons comprising the steps of:
   (a) adding said alkane or hydrocarbon to a mixed aqueous-organic solvent in the presence of oxygen;
   (b) adding a ruthenium metal complex, activated by an end-oxo group, said catalyst having the formula LRu-), where L is a Schiff or a substituted Schiff base;
   (c) or a bridging-oxo group said catalyst having the formula:

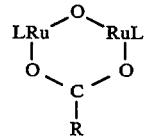

wherein L is a Schiff base or a substituted Schiff base and R is H or alkyl (C40) or an aryl (CL30).

(d) and at least one carboxylato group to the solvent system in a concentration range of $10^3$ to $10^{-6}$ moles of catalyst per liter of solution and
   (e) where the temperature ranges between 20°-60° C. and the pressure ranges between 5-20 atmospheres.

14. The process as claimed in claim 13, wherein said temperature is 30° C. and said pressure is 14 atmosphere of $CH_4:O_2$.

15. The process as claimed in claim 14, wherein said alkane is methane.

16. The process as claimed in claim 15, wherein said ruthenium metal complex is coordinated with a Schiff base or a substituted Schiff base.

* * * * *

UNITED STATES PATENT AND TRADEMARK OFFICE
CERTIFICATE OF CORRECTION

PATENT NO.   : 5,347,057
DATED        : September 13, 1994
INVENTOR(S)  : Mirza Mohammad Taqui Khan It is certified that error appears in the above-identified patent and that said Letters Patent is hereby corrected as shown below:

Column 5, line 44, Claim 4, "that selectively" should read --that are selectively--;

Column 6, line 25, Claim 13, "LRu-)," should read --LRu-O,--.

Signed and Sealed this

Twentieth Day of December, 1994

Attest:

BRUCE LEHMAN

Attesting Officer   Commissioner of Patents and Trademarks